US009833419B2

(12) United States Patent
Mantelle

(10) Patent No.: US 9,833,419 B2
(45) Date of Patent: *Dec. 5, 2017

(54) TRANSDERMAL ESTROGEN DEVICE AND DELIVERY

(71) Applicant: NOVEN PHARMACEUTICALS, INC., Miami, FL (US)

(72) Inventor: Juan Mantelle, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/870,574

(22) Filed: Sep. 30, 2015

(65) Prior Publication Data

US 2016/0015655 A1 Jan. 21, 2016

Related U.S. Application Data

(63) Continuation of application No. 14/738,255, filed on Jun. 12, 2015, which is a continuation of application No. 14/024,985, filed on Sep. 12, 2013, now Pat. No. 9,724,310, which is a continuation of application No. 13/553,972, filed on Jul. 20, 2012, now Pat. No. 9,730,900, which is a continuation of application No. 12/216,811, filed on Jul. 10, 2008, now Pat. No. 8,231,906.

(51) Int. Cl.

| | |
|---|---|
| ***A61K 9/70*** | (2006.01) |
| ***A61K 31/565*** | (2006.01) |
| ***A61K 9/00*** | (2006.01) |
| ***A61K 47/10*** | (2017.01) |
| ***A61K 47/32*** | (2006.01) |

(52) U.S. Cl.

CPC .......... *A61K 9/7069* (2013.01); *A61K 9/0014* (2013.01); *A61K 9/7061* (2013.01); *A61K 31/565* (2013.01); *A61K 47/10* (2013.01); *A61K 47/32* (2013.01)

(58) Field of Classification Search

None

See application file for complete search history.

(56) References Cited

U.S. PATENT DOCUMENTS

| | | | | |
|---|---|---|---|---|
| 4,390,520 | A | 6/1983 | Nagai et al. | |
| 4,494,278 | A | 1/1985 | Kroyer et al. | |
| 4,559,222 | A | 12/1985 | Enscore et al. | |
| 4,585,836 | A | 4/1986 | Homan et al. | |
| 4,591,622 | A | 5/1986 | Blizzard et al. | |
| 4,624,665 | A * | 11/1986 | Nuwayser | A61K 9/7084 424/448 |
| 4,655,767 | A | 4/1987 | Woodard et al. | |
| 4,746,515 | A | 5/1988 | Cheng et al. | |
| 4,769,028 | A | 9/1988 | Hoffmann et al. | |
| 4,814,168 | A | 3/1989 | Sablotsky et al. | |
| 4,911,707 | A | 3/1990 | Heiber et al. | |
| 4,915,950 | A | 4/1990 | Miranda et al. | |
| 4,938,759 | A | 7/1990 | Enscore et al. | |
| 4,983,395 | A | 1/1991 | Chang et al. | |
| 4,994,267 | A | 2/1991 | Sablotsky | |
| 4,994,278 | A | 2/1991 | Sablotsky et al. | |
| 5,151,271 | A | 9/1992 | Otsuka et al. | |
| 5,271,940 | A | 12/1993 | Cleary et al. | |
| 5,300,291 | A | 4/1994 | Sablotsky et al. | |
| 5,350,581 | A | 9/1994 | Kochinke | |
| 5,446,070 | A | 8/1995 | Mantelle | |
| 5,474,783 | A | 12/1995 | Miranda et al. | |
| 5,474,787 | A | 12/1995 | Gray et al. | |
| 5,505,956 | A | 4/1996 | Kim et al. | |
| 5,567,488 | A | 10/1996 | Allen et al. | |
| 5,584,355 | A | 12/1996 | Burns | |
| RE35,474 | E | 3/1997 | Woodard et al. | |
| 5,656,286 | A | 8/1997 | Miranda et al. | |
| 5,665,377 | A | 9/1997 | Gonella | |
| 5,730,999 | A | 3/1998 | Lehmann et al. | |
| 5,762,952 | A | 6/1998 | Barnhart et al. | |
| 5,837,280 | A | 11/1998 | Kenealy et al. | |
| 5,902,603 | A | 5/1999 | Chen et al. | |
| 5,904,931 | A | 5/1999 | Lipp et al. | |
| 5,906,830 | A | 5/1999 | Farinas et al. | |
| 5,928,666 | A | 7/1999 | Farinas et al. | |
| 5,958,446 | A | 9/1999 | Miranda et al. | |
| 6,024,976 | A | 2/2000 | Miranda et al. | |
| 6,156,335 | A | 12/2000 | Rovati et al. | |
| 6,221,383 | B1 | 4/2001 | Miranda et al. | |
| 6,235,306 | B1 | 5/2001 | Miranda et al. | |
| 6,337,086 | B1 | 1/2002 | Kanios et al. | |
| 6,562,363 | B1 | 5/2003 | Mantelle et al. | |
| 6,638,528 | B1 * | 10/2003 | Kanios | A61K 9/7069 424/443 |
| 6,808,739 | B2 | 10/2004 | Sitz et al. | |

(Continued)

FOREIGN PATENT DOCUMENTS

EP 0 887 075 A2 12/1998

OTHER PUBLICATIONS

Toole et al., "Evaluation of irritation and sensitisation of two 50 μg/day oestrogen patches," Maturitas, vol. 43, pp. 257-263, Dec. 2002.

Marty, "New trends in transdermal technologies: Development of the skin patch, Menorest®," International Journal of Gynecology & Obstetrics, vol. 52, Suppl. 1, pp. S17-S20, Mar. 1996.

Mantelle, "DOT Matrix® Technology," Modified-Release Drug Technology, Rathbone et al., eds., Chapter 30, pp. 405-415, May 28, 2008.

Novartis, "Estraderm®," Prescribing information, Jun. 2004.

Novartis, "Vivelle®," Prescribing information, Jun. 2004.

Novartis, "Vivelle-Dot®," Prescribing information, Jun. 2004.

Bayer Healthcare, "Climara®," Prescribing information, 2007.

3M Pharmaceuticals, "Menostar™," Prescribing information, Jun. 2004.

Watson Pharma, Inc., "Alora®," Prescribing information, May 2005.

(Continued)

*Primary Examiner* — Melissa Fisher

(74) *Attorney, Agent, or Firm* — Foley & Lardner LLP

(57) ABSTRACT

Described are transdermal drug delivery systems for the transdermal administration of estrogen, comprising a polymer matrix and estrogen. Methods of making and using such systems also are described.

15 Claims, 1 Drawing Sheet

(56) References Cited

U.S. PATENT DOCUMENTS

| | | | |
|---|---|---|---|
| 7,456,159 | B2 | 11/2008 | Houze et al. |
| 8,231,906 | B2 | 7/2012 | Mantelle |
| 8,343,538 | B2 | 1/2013 | Kanios et al. |
| 9,724,310 | B2 | 8/2017 | Mantelle |
| 9,730,900 | B2 | 8/2017 | Mantelle |
| 2002/0100185 | A1 | 8/2002 | Sitz et al. |
| 2003/0099695 | A1 | 5/2003 | Mueller |
| 2003/0228354 | A1 | 12/2003 | Muraoka et al. |
| 2005/0129749 | A1 | 6/2005 | Strauss |
| 2005/0169977 | A1 | 8/2005 | Kanios |
| 2005/0202073 | A1 | 9/2005 | Jackson et al. |
| 2006/0078602 | A1 | 4/2006 | Kanios |
| 2006/0233870 | A1 | 10/2006 | Houze et al. |
| 2006/0240087 | A1 | 10/2006 | Houze et al. |
| 2009/0041831 | A1 | 2/2009 | Miller et al. |
| 2013/0156815 | A1 | 6/2013 | Mantelle |
| 2014/0200530 | A1 | 7/2014 | Mantelle |
| 2015/0272905 | A1 | 10/2015 | Mantelle |

OTHER PUBLICATIONS

Serono Laboratories, Inc., "Esclim®," Prescribing information, Aug. 1998.
Office Action dated May 5, 2016 in U.S. Appl. No. 14/024,985 (US 2014-0200530).
Notice of Allowance dated Sep. 15, 2016 in U.S. Appl. No. 14/024,985 (US 2014-0200530).
Notice of Allowance dated Jan. 10, 2017 in U.S. Appl. No. 14/024,985 (US 2014-0200530).
Office Action dated May 5, 2016 in U.S. Appl. No. 13/553,972 (US 2013-0156815).
Notice of Allowance dated Aug. 26, 2016 in U.S. Appl. No. 13/553,972 (US 2013-0156815).
Notice of Allowance dated Dec. 9, 2016 in U.S. Appl. No. 13/553,972 (US 2013-0156815).
Office Action dated Apr. 29, 2016 in U.S. Appl. No. 14/738,255 (US 2015-0272905).
Decision in European Opposition issued on Feb. 14, 2017 in application No. EP 09 790 211.8.
Vaughan, "Using Solubility Parameters in Cosmetics Formulation," *J. Soc. Cosmet. Chem.*, vol. 36, pp. 319-333 (1985).
Sobieski et al., "Silicone Pressure Sensitive Adhesives," *Handbook of Pressure-Sensitive Adhesive Technology*. 2$^{nd}$ ed., pp. 508-517 (D. Satas, ed.), Van Nostrand Reinhold, New York (1989).
"Acrylic Adhesives," *Handbook of Pressure-Sensitive Adhesive Technology*, 2$^{nd}$ ed., pp. 396-456 (D. Satas, ed.), Van Nostrand Reinhold, N.Y. (1989).
Nagai et al., "New Drug Delivery Systems," Kurashiki Printing Co. Ltd., Academic Document 2009-00984-005, published Jan. 31, 2000.
Sekine et al, "New Cosmetic Handbook," Nikko Chemical Co. Ltd., et al., Academic Documents 2008-02180-001, published Oct. 30, 2006.
Novartis Pharmaceuticals Corporation, "Vivelle-Dot® (estradiol transdermal system)," prescription labeling, Aug. 2004.
Benson, "Transdermal Drug Delivery: Penetration Enhancement Techniques," Current Drug Delivery, vol. 2, pp. 23-33, 2005.
Feldmann et al, "Percutaneous Penetration of Steroids in Man," The Journal of Investigative Dermatology, vol. 52, No. 1, pp. 89-94, 1969.
Schaefer et al., "Contraception via Topical Application? A Review," Contraception, vol. 20, No. pp. 225-236, Sep. 1979.
International Preliminary Report on Patentability and Written Opinion dated Apr. 19, 2007.
International Search Report dated Apr. 6, 2005 in application No. PCT/US2004/029789.
International Search Report dated Feb. 24, 2011 in application No. PCT/US2009/050069.
"Acrylic and Methacrylic Ester Polymers," *Polymer Science and Engineering*, vol. 1, 2$^{nd}$ ed., pp. 234-269, John Wiley & Sons (1984).
Office Action dated Sep. 9, 2010 by the Examiner in U.S. Appl. No. 12/216,811 (now U.S. Pat. No. 8,231,906).
Office Action dated Jan. 20, 2011 by the Examiner in U.S. Appl. No. 12/216,811 (now U.S. Pat. No. 8,231,906).
Office Action dated Jun. 30, 2011 by the Examiner in U.S. Appl. No. 12/216,811 (now U.S. Pat. No. 8,231,906).
Office Action dated Sep. 13, 2011 by the Examiner in U.S. Appl. No. 12/216,811 (now U.S. Pat. No. 8,231,906).
Office Action dated Nov. 8, 2011 by the Examiner in U.S. Appl. No. 12/216,811 (now U.S. Pat. No. 8,231,906).
Office Action dated May 29, 2012 by the Examiner in U.S. Appl. No. 12/216,811 (now U.S. Pat. No. 8,231,906).
Notice of Allowance dated Jun. 19, 2012 by the Examiner in U.S. Appl. No. 12/216,811 (now U.S. Pat. No. 8,231,906).
Office Action dated Dec. 29, 2010 by the Examiner in U.S. Appl. No. 11/245,084 (now U.S. Pat. No. 8,343,538).
Office Action dated Apr. 14, 2010 by the Examiner in U.S. Appl. No. 11/245,084 (now U.S. Pat. No. 8,343,538).
Office Action dated Jun. 10, 2009 by the Examiner in U.S. Appl. No. 11/245,084 (now U.S. Pat. No. 8,343,538).
Office Action dated Oct. 26, 2011 by the Examiner in U.S. Appl. No. 11/245,084 (now U.S. Pat. No. 8,343,538).
Office Action dated May 13, 2011 by the Examiner in U.S. Appl. No. 11/245,084 (now U.S. Pat. No. 8,343,538).
Office Action dated Jun. 13, 2012 by the Examiner in U.S. Appl. No. 11/245,084 (now U.S. Pat. No. 8,343,538).
Notice of Allowance dated Aug. 22, 2012 by the Examiner in U.S. Appl. No. 11/245,084 (now U.S. Pat. No. 8,343,538).
Office Action dated Apr. 12, 2013 by the Examiner in U.S. Appl. No. 13/553,972 (US 2013/0156815).
Office Action dated Sep. 4, 2013 by the Examiner in U.S. Appl. No. 13/553,972 (US 2013/0156815).
Office Action dated Mar. 5, 2014 by the Examiner in U.S. Appl. No. 13/553,972 (US 2013/0156815).
Office Action dated May 5, 2015 by the Examiner in U.S. Appl. No. 13/553,972 (US 2013/0156815).
Notice of Allowance dated Oct. 2, 2015 by the Examiner in U.S. Appl. No. 13/553,972 (US 2013/0156815).
Office Action dated May 20, 2015 by the Examiner in U.S. Appl. No. 14/024,985 (US 2014/0200530).
Notice of Allowance dated Oct. 2, 2015 by the Examiner in U.S. Appl. No. 14/024,985 (US 2014/0200530).
Office Action dated Aug. 12, 2015 by the Examiner in U.S. Appl. No. 14/738,255 (US 2015/0272905).
Office Action dated Oct. 26, 2015 by the Examiner in U.S. Appl. No. 14/738,255 (US 2015/0272905).
Rietschel et al, "Effects of harvesting techniques on hydration dynamics: gravimetric studies of stratum corneum," J. Soc. Cosmet. Chem., vol. 29, pp. 777-782, Dec. 1978.
Feldstein et al., "Modeling of percutaneous drug transport in vitro using skin-imitating Carbosil membrane," Journal of Controlled Release, vol. 52, pp. 25-40, 1998.
Pfister, "Transdermal and Dermal Therapeutic Systems: Current Status," Transdermal and Topical Drug Delivery Systems, Ghosh et al., eds., Chapter 2, pp. 33-112, 1997.
Dow Corning, :"Dow Corning® BIO-PSA Standard Silicone Adhesives," Product Information, Jul. 28, 2008.
Janisch et al., Email correspondence, Mar. 10, 2016.
Manngold, Apr. 28, 2004 letter to Angela Nwaneri re: Duro-Tak® 87-4287 and 87-2287.
Noven Pharmaceuticals, Inc., Response filed in European application No. 09790211.8 dated Dec. 19, 2014.
Mantelle et al., "Effect of Silicone/Acrylic PSA Blends on Skin Permation," Proceed. Int'l. Symp. Control. Rel. Bioact. Mater., Jun. 20-23, 1999.
Notice of Allowance dated Mar. 23, 2017 in U.S. Appl. No. 13/553,972 (US 2013/0156815).
Notice of Allowance dated Apr. 26, 2017 in U.S. Appl. No. 14/024,985 (US 2014/0200530).

(56) References Cited

OTHER PUBLICATIONS

Notice of Allowance dated Jun. 27, 2017 in U.S. Appl. No. 13/553,972 (US 2013/0156815).

Notice of Allowance dated Jun. 27, 2017 in U.S. Appl. No. 14/024,985 (US 2014/0200530).

* cited by examiner

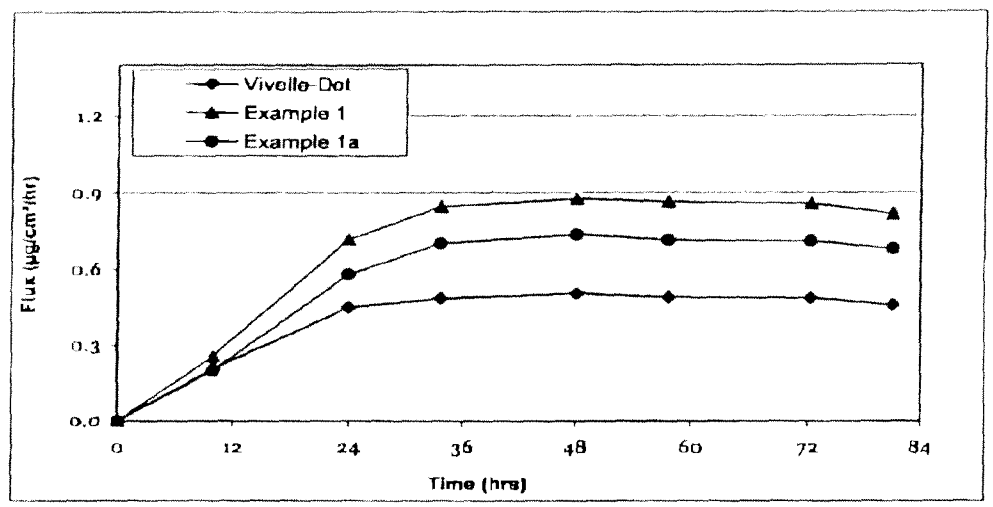
Vivelle-Dot
Example 1
Example 1a
Flux (µg/cm²/hr)
0.0
0.3
0.6
0.9
1.2
0
12
24
36
48
60
72
84
Time (hrs)

TRANSDERMAL ESTROGEN DEVICE AND DELIVERY

FIELD OF THE INVENTION

Described herein are compositions and methods for the transdermal delivery of estrogen.

BACKGROUND

This invention relates generally to transdermal drug delivery systems, and more particularly, to transdermal drug delivery systems for the delivery of estrogen. The use of a transdermal system, for example, a patch comprising a pressure-sensitive adhesive containing a drug, as a means of delivering drug through the skin is well known. However, there remains a need for transdermal drug delivery systems designed for the delivery of specific drugs, such as estrogen, and there remains a particular need for smaller transdermal drug delivery systems that exhibit desired pharmacokinetic properties.

Transdermal delivery systems (adhesive patches) as dosage forms have been the subject of a vast number of patent applications over the last 25 years, yielding many patents but few commercial products in comparison. To those working in the field, the relatively small number of commercial products is not surprising. Although regulatory, economic, and market hurdles play a role in limiting the number of products on the market, the task of developing a transdermal delivery system that achieves desired physical and pharmacokinetic parameters to satisfy physician and patient demand is more daunting. Parameters to be considered during commercial product development may include drug solubility, drug stability (e.g., as may arise from interaction with other component materials and/or the environment), delivery of a therapeutic amount of drug at a desired delivery rate over the intended duration of use, adequate adhesion at the anatomical site of application, integrity (e.g., minimal curling, wrinkling, delaminating and slippage) with minimal discomfort, irritation and sensitization both during use and during and after removal, and minimal residual adhesive (or other components) after removal. Size also may be important from a manufacturing and patient viewpoint, and appearance may be important from a patient viewpoint. The physical manufacturing and production aspects of commercial product development (e.g., the identity and costs of materials, equipment, and labor) and supporting analytical methods required for regulatory compliance also can be significant.

Of the physical parameters that are considered when developing a commercial transdermal drug delivery system, size, e.g., surface area at the site of application, is often dictated and limited by other physical and pharmacokinetic requirements, such as desired drug delivery rates and daily dosages. In general, it is easier to develop a relatively "large" transdermal drug delivery system that will achieve drug delivery at target therapeutic levels over an intended duration of therapy, than it is to develop a smaller transdermal drug delivery system that still exhibits acceptable pharmacokinetic properties. Still, because size directly impacts costs (e.g., costs of component materials, costs of packaging materials, costs for production and manufacturing equipment, labor costs relative to product yield per run time, etc.) and patients generally prefer smaller systems to larger ones (both for aesthetic reasons and comfort, since a smaller surface may permit the use of less aggressive adhesives), there is a need for smaller transdermal drug delivery systems.

SUMMARY

In accordance with one embodiment, there is provided a transdermal drug delivery system comprising a drug containing layer defining an active surface area and comprising a polymer matrix comprising estradiol, wherein the system includes greater than 0.156 mg/cm$^2$ estradiol and achieves an estradiol flux that is greater than 0.01 mg/cm$^2$/day, based on the active surface area. In some embodiments, the polymer matrix comprises a polymer blend comprising an acrylic adhesive, a silicone adhesive, and soluble PVP. In some embodiments, the polymer matrix comprises about 2-25% by weight acrylic adhesive, about 45-70% by weight silicone adhesive, about 2-25% by weight soluble PVP, about 5-15% penetration enhancer, and about 0.1-10% by weight estradiol, all based on the total dry weight of the polymer matrix. In some embodiments, the polymer matrix comprises about 20% by weight acrylic adhesive, about 56.9% by weight silicone adhesive, about 7.5% by weight soluble PVP, about 6.0% by weight oleyl alcohol, about 8.0% by weight dipropylene glycol, and about 1.6% by weight estradiol. In some embodiments, the acrylic adhesive and silicone adhesive are present in a ratio of from about 1:2 to about 1:6, based on the total weight of the acrylic and silicone adhesives.

In some embodiments, the penetration enhancer comprises oleyl alcohol or dipropylene glycol, or both.

In some embodiments, the polymer matrix comprises an amount of estradiol effective to deliver a therapeutically effective amount of estradiol over a period of time selected from the group consisting of at least 1 day, at least 2 days, at least 3 days, at least 4 days, at least 5 days, at least 6 days and at least 7 days. In some embodiments, the polymer matrix comprises an amount of estradiol effective to deliver an amount of estradiol selected from the group consisting of about 0.025, 0.0375, 0.05, 0.075 and 0.1 mg/day.

In some embodiments, the polymer matrix has a coat weight of greater than about 10 mg/cm$^2$. In some embodiments, the polymer matrix has a coat weight selected from the group consisting of about 12.5 and about 15 mg/cm$^2$.

In accordance with some embodiments, there is provided a transdermal drug delivery system comprising a polymer matrix comprising estradiol, wherein the system has an active surface area that is about 60% of a size selected from the group consisting of 2.5, 3.75, 5.0, 7.5 and 10.0 cm$^2$ and is effective to deliver an amount of estradiol per day of about 0.025, 0.0375, 0.05, 0.075 and 0.1 mg/day, respectively.

In accordance with some embodiments, there is provided a method for administering estradiol, comprising applying to the skin or mucosa of a subject in need thereof a transdermal drug delivery system comprising a drug-containing layer defining an active surface area and comprising a polymer matrix comprising estradiol, wherein the system includes greater than 0.156 mg/cm$^2$ estradiol and achieves an estradiol flux that is greater than 0.01 mg/cm$^2$/day, based on the active surface area. In some embodiments, the system has an active surface area that is about 60% of a size selected from the group consisting of 2.5, 3.75, 5.0, 7.5 and 10.0 cm$^2$ and is effective to deliver an amount of estradiol per day of about 0.025, 0.0375, 0.05, 0.075 and 0.1 mg/day, respectively.

In accordance with some embodiments, there is provided a method of making a transdermal drug delivery system for administering estrogen, comprising forming a polymer matrix comprising estrogen and a polymer blend comprising an acrylic adhesive, a silicone adhesive, and soluble PVP, and applying the polymer matrix to a support layer such that the system includes greater than 0.156 mg/cm$^2$ estradiol. In some embodiments, the system has an active surface area that is about 60% of a size selected from the group consisting of 2.5, 3.75, 5.0, 7.5 and 10.0 cm$^2$. In some embodiments, the polymer matrix comprises about 20% by weight acrylic adhesive, about 56.9% by weight silicone adhesive, about 7.5% by weight soluble PVP, about 6.0% by weight oleyl alcohol, about 8.0% by weight dipropylene glycol, and about 1.6% by weight estradiol. In some embodiments, the polymer matrix is applied to the support layer at a coat weight of greater than about 10 mg/cm$^2$. In some embodiments, the polymer matrix coat weight is selected from the group consisting of about 12.5 and about 15 mg/cm$^2$.

BRIEF DESCRIPTION OF THE DRAWINGS

FIG. 1 illustrates the estradiol flux (μg/cm$^2$/hr) over time (0-81 hours) from transdermal delivery systems according to the invention (▲ & ●), as compared to Vivelle-Dot® (♦).

DETAILED DESCRIPTION

The field of transdermal delivery systems suffers from the problem of needing to balance many different competing factors to develop a commercial product that exhibits, for example both clinical efficacy and satisfactory wear properties while remaining acceptable to patients. For example, when selecting the size of a transdermal delivery system, it is necessary to balance factors that favor a smaller size (such as lower cost, better adhesive performance and improved aesthetics) against factors that favor a larger size (such as the target delivery rate (flux) and daily dose). The Vivelle-Dot® transdermal estradiol product (manufactured by Noven Pharmaceuticals Inc.) is available in five different active surface areas (2.5, 3.75, 5.0, 7.5 and 10.0 cm$^2$) which each deliver different amounts of drug per day (0.025, 0.0375, 0.05, 0.075 and 0.1 mg/day, respectively). Each of the Vivelle-Dot® products include 0.156 mg/cm$^2$ estradiol.

In accordance with some embodiments, the present invention provides transdermal drug delivery systems for the transdermal delivery of estrogen that have a smaller active surface area than Vivelle-Dot® but achieve daily dosages that are about equal to or greater than the Vivelle-Dot® products. For example, the present invention includes transdermal drug delivery systems that achieve daily dosages that are about equal to a Vivelle-Dot® product, in a smaller sized system. The ability to provide a smaller system without sacrificing daily dosage represents a significant advance.

Applicant surprisingly discovered that increasing the coat weight of the drug-containing adhesive layer resulted in an increased flux per unit area, and thus permitted the development of smaller transdermal drug delivery systems that achieve comparable daily dosages. This result was surprising because coat weight is typically selected to control the duration of delivery, but is not generally understood to impact delivery rate. Thus, while it is known in the art to increase coat weight to provide delivery over a longer period of time, it was not known that increasing coat weight could increase delivery rate or flux, and thus permit the development of a smaller system while maintaining daily dosage.

In accordance with some aspects, there are provided transdermal drug delivery systems and methods for the transdermal delivery of estrogen. In specific embodiments, the systems exhibit increased flux than other known estrogen devices (such as Vivelle-Dot®, manufactured by Noven Pharmaceuticals Inc.) and, therefore, exhibit increased drug delivery per unit area. For example, in some embodiments, the systems exhibit a flux greater than the 0.01 mg/cm$^2$/day exhibited by the Vivelle-Dot® products, such as a flux that is about 1.25, 1.33, 1.5, 1.67, 1.75, 2, 3, 4, or 5 times the flux of the Vivelle-Dot® products. In some embodiments, the systems have a greater coat weight than other known estrogen devices. For example, in some embodiments, the systems have a coat weight such that the amount of estradiol per unit area is greater than the 0.156 mg/cm$^2$ estradiol of the Vivelle-Dot® products, such as a coat weight that is about 1.25, 1.33, 1.5, 1.67, 1.75, 2, or 3 times the coat weight of the Vivelle-Dot® products, or greater. Thus, in accordance with some aspects, the invention permits the use of smaller devices to achieve comparable drug delivery.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described composition (e.g., transdermal drug delivery system, polymer matrix, etc.) comprises less than about 5%, less than about 3%, or less than about 1% by weight, based on the total weight of the composition at issue, of the excluded component.

As used herein "subject" denotes any animal in need of drug therapy, including humans. For example, a subject may be suffering from or at risk of developing a condition that can be treated or prevented with estrogen, or may be taking estrogen for health maintenance purposes.

As used herein, the phrases "therapeutically effective amount" and "therapeutic level" mean that drug dosage or plasma concentration in a subject, respectively, that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing layer of the transdermal drug delivery system.

As used herein, "coat weight" refers to the weight of the drug-containing layer per unit area of the active surface area of the transdermal drug delivery system.

As used herein, "estrogen" includes estrogenic steroids such as estradiol (17-β-estradiol), estradiol benzoate, estradiol 17β-cypionate, estropipate, equilenin, equilin, estriol, estrone, ethinyl estradiol, conjugated estrogens, esterified estrogens, and mixtures thereof.

As used herein, "flux" (also called "permeation rate") is defined as the absorption of a drug through skin or mucosal tissue, and is described by Fick's first law of diffusion:

$$J=-D(\mathrm{dCm/dx})$$

where J is the flux in $g/cm^2/sec$, D is the diffusion coefficient of the drug through the skin or mucosa in $cm^2/sec$ and dCm/dx is the concentration gradient of the drug across the skin or mucosa.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases estrogen upon application to the skin (or any other surface noted above). A transdermal drug delivery system may comprise a backing layer, a drug-containing layer, and a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. As described below, in one embodiment, the transdermal drug delivery system comprises a drug-containing polymer matrix that comprises a pressure-sensitive adhesive or bioadhesive, and is adopted for direct application to a user's (e.g., a subject's) skin. In other embodiments, the polymer matrix is non-adhesive and may be provided with separate adhesion means (such as a separate adhesive layer) for application and adherence to the user's skin.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se, or if it functions as an adhesive by the addition of tackifiers, plasticizers, crosslinking agents or other additives. Thus, in some embodiments, the polymer matrix comprises a pressure-sensitive adhesive polymer or a bioadhesive polymer, with estrogen dissolved or dispersed therein. The polymer matrix also may comprise tackifiers, plasticizers, crosslinking agents or other additives described herein. U.S. Pat. No. 6,024,976 describes polymer blends that are useful in accordance with the transdermal systems described herein. The entire contents of U.S. Pat. No. 6,024,976 is incorporated herein by reference.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB), of different molecular weights, wherein each resultant mixture is a pressure-sensitive adhesive. In the last case, the polymers of lower molecular weight in the mixture are not considered to be "tackifiers," said term being reserved for additives which differ other than in molecular weight from the polymers to which they are added.

In some embodiments, the polymer matrix is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

As used herein, the term "rubber-based pressure-sensitive adhesive" refers to a viscoelastic material which has the properties of a pressure-sensitive adhesive and which contains at least one natural or synthetic elastomeric polymer.

In some embodiments, the transdermal drug delivery system includes one or more additional layers, such as one or more additional polymer matrix layers, or one or more adhesive layers that adhere the transdermal drug delivery system to the user's skin. In other embodiments, the transdermal drug delivery system is monolithic, meaning that it comprises a single polymer matrix layer comprising a pressure-sensitive adhesive or bioadhesive with drug dissolved or dispersed therein, and no rate-controlling membrane.

The transdermal drug delivery system also may include a drug impermeable backing layer or film. In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers.

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-off® 7610 and 3M's 1022 Scotch Pak.

A used herein, a "monolithic" transdermal drug delivery system may include a backing layer and/or release liner.

In accordance with some embodiments, the transdermal dug delivery system comprises a drug-containing polymer matrix layer that comprises a pressure-sensitive adhesive blend comprising an acrylic polymer, a silicone polymer, and a soluble PVP.

Acrylic Polymers

The term "acrylic polymer" is used here as in the art interchangeably with "polyacrylate," "polyacrylic polymer," and "acrylic adhesive." The acrylic-based polymers can be any of the homopolymers, copolymers, terpolymers, and the like of various acrylic acids or esters. In some embodiments, the acrylic-based polymers are adhesive polymers. In other embodiments, the acrylic-based polymers function as an adhesive by the addition of tackifiers, plasticizers, crosslinking agents or other additives.

The acrylic polymer can include copolymers, terpolymers and multipolymers. For example, the acrylic polymer can be any of the homopolymers, copolymers, terpolymers, and the like of various acrylic acids. In some embodiments, the acrylic polymer constitutes from about 2% to about 95% by weight of the polymer content of the polymer matrix, including about 3% to about 90% and about 5% to about 85%, such as 2% to 95%, 3% to 90% and 5% to 85%. In some embodiments, the amount and type of acrylic polymer is dependent on the type and amount of estrogen used.

Acrylic polymers useful in practicing the invention include polymers of one or more monomers of acrylic acids and other copolymerizable monomers. The acrylic polymers also include copolymers of alkyl acrylates and/or methacrylates and/or copolymerizable secondary monomers or monomers with functional groups. Combinations of acrylic-based polymers based on their functional groups is also contemplated. Acrylic-based polymers having functional groups include copolymers and terpolymers which contain, in addition to nonfunctional monomer units, further monomer units having free functional groups. The monomers can be monofunctional or polyfunctional. By varying the amount of each type of monomer added, the cohesive properties of the resulting acrylic polymer can he changed as is known in the art. In some embodiments, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid and methacrylic acid and alkyl acrylic or methacrylic esters such as methyl acrylate, ethyl acrylate, propyl acrylate, amyl acrylate, butyl acrylate, butyl methacrylate, hexyl acrylate, hexyl methacrylate, heptyl acrylate, octyl acrylate, nonyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, glycidyl acrylate, and corresponding methacrylic esters.

Non-functional acrylic-based polymers can include any acrylic based polymer having no or substantially no free functional groups.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

As used herein, "functional monomers or groups," are monomer units typically in acrylic-based polymers which have reactive chemical groups which modify the acrylic-based polymers directly or which provide sites for further reactions. Examples of functional groups include carboxyl, epoxy, hydroxyl, sulfoxyl, and amino groups. Acrylic-based polymers having functional groups contain, in addition to the nonfunctional monomer units described above, further monomer units having free functional groups. The monomers can be monofunctional or polyfunctional. These functional groups include carboxyl groups, hydroxy groups, amino groups, amido groups, epoxy groups, etc. Typical carboxyl functional monomers include acrylic acid, methacrylic acid, itaconic acid, maleic acid, and crotonic acid. Typical hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. As noted above, in some embodiments, the acrylic polymer does not include such functional groups.

Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989); "Acrylic and Methacrylic Ester Polymers," *Polymer Science and Engineering,* Vol. 1, 2nd ed., pp 234-268, John Wiley & Sons, (1984); U.S. Pat. No. 4,390,520; and U.S. Pat. No. 4,994,267, all of which are expressly incorporated by reference in their entireties.

Suitable acrylic polymers also include pressure-sensitive adhesives which are commercially available, such as the acrylic-based adhesives sold under the trademarks DURO-TAK® by National Starch and Chemical Corporation, Bridgewater, N.J. (such as DURO-TAK® 87-2287, -4098, -2852, -2196, -2296, -2194, -2516, -2070, -2353, -2154, -2510, -9085, -9088 and 73-9301). Other suitable acrylic adhesives include those sold under the trademark EUDRAGIT® by Roehm Pharma GmbH, Darmstadt, Germany, those sold by Cytec Surface Specialties, St. Louis, Mo., under the trademarks GELVA® Multipolymer Solution (such as GELVA® 2480, 788, 737, 263, 1430, 1753, 1151, 2450, 2495, 3067, 3071, 3087 and 3235). For example, hydroxy functional adhesives with a reactive functional OH group in the polymeric chain, can be used. Non-limiting commercial examples of this type of adhesives include both GELVA® 737, 788, and 1151, and DURO-TAK® 87-2287, -4287, -2510 and -2516.

Silicon Polymers

The term "silicone-based" polymer is used interchangeably with the terms siloxane, polysiloxane, and silicones as used herein and as known in the art. A suitable silicone-based polymer may also be a pressure-sensitive adhesive. Thus, in some embodiments, the silicone-based polymer is an adhesive polymer. In other embodiments, the silicone-based polymer functions as an adhesive by the addition of tackifiers, plasticizers, crosslinking agents, or other additives.

Suitable polysiloxanes include silicone pressure-sensitive adhesives which are based on two major components: (i) a polymer or gum and (ii) a tackifying resin. A polysiloxane adhesive can be prepared by cross-linking a gum, typically a high molecular weight polydiorganosiloxane, with a resin, to produce a three-dimensional silicate structure, via a condensation reaction in an appropriate organic, volatile solvent, such as ethyl acetate or heptane. The ratio of resin to polymer can be adjusted in order to modify the physical properties of polysiloxane adhesives. Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989).

Exemplary silicone-based polymers are adhesives (e.g., capable of sticking to the site of topical application), including pressure-sensitive adhesives. Illustrative examples of silicone-based polymers having reduced silanol concentrations include silicone-based adhesives (and capped polysiloxane adhesives) such as those described in U.S. Pat. No. Re. 35,474 and U.S. Pat. No. 6,337,086, which are incorporated herein by reference in their entireties, and which are commercially available from Dow Corning Corporation (Dow Corning Corporation, Medical Products, Midland, Mich.) as BIO-PSA® 7-4100, -4200 and -4300 product series, and non-sensitizing, pressure-sensitive adhesives produced with compatible organic volatile solvents (such as ethyl acetate or heptane) and available commercially under their BIO-PSA® 7-4400 series, -4500 series and -4600 series.

Further details and examples of silicone pressure-sensitive adhesives which are useful in the polymer matrices and compositions and methods described herein are mentioned in the following U.S. Pat. Nos.: 4,591,622; 4,584,355; 4,585,836; and 4,655,767, which are all expressly incorporated by reference herein in their entireties. It should also be understood that silicone fluids are also contemplated for use in the polymer matrices and methods described herein.

In some embodiments, the polysiloxane constitutes from about 9% to about 97% of the polymer content of the polymer matrix, including about 8% to about 97% and about 14% to about 94%, such as 9% to 97%, 8% to 97%, and 14% to 94%, Soluble PVP In some embodiments, the polymer matrix includes soluble PVP. Soluble PVP has been found to be highly effective in preventing crystallization of drugs, such as estradiol, in adhesive-type transdermal drug delivery system. Soluble PVP also may modulate the transdermal permeation rate of the drug.

The term "PVP or "polyvinylpyrrolidone" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. See, generally, Buhler, KOLLIDON.RTM.: POLYVINYLPRYRROLIDONE FOR THE PHARMACEUTICAL INDUSTRY, BASF Aktiengesellschaft (1992).

The amount and type of soluble PVP used may depend on the quantity and type of estrogen present, as well as the type of adhesive, but can be readily determined through routine experimentation. Typically, the PVP is present in an amount from about 1% to about 20% by weight, preferably from about 5% to about 15% by weight, based on the total weight of the polymer matrix. However, the amount of PVP can be higher than 20% for example, up to 40%, depending on the particular drug used and on the desired properties of the blend. The soluble PVP may have a molecular weight of about 2,000 to 1,100,000, including 5,000 to 100,000, and 7,000 to 54,000. In some embodiments, the soluble PVP has a molecular weight of from about 17,000 to about 90,000, such as from about 17,000 to about 60,000, including from 17,000 to 90,000 and from 17,000 to 60,000.

In some embodiments, the polymer matrix comprises a soluble PVP with a rubber-based pressure-sensitive adhesive and a polyacrylate polymer, such as a blend of an acrylic polymer, a polysiloxane and a soluble PVP. In some embodiments, the blend is chosen to affect the rate of drug delivery. More specifically, a plurality of polymers including a soluble polyvinylpyrrolidone, which may have different solubility parameters for the drug and which may he immiscible with each other, may be selected to adjust the solubility of the drug in the polymer matrix, thereby controlling the maximum concentration of the drug in the system, and modulating drug delivery through the dermis.

The amount of acrylic-based polymer and silicone-based polymer can be adjusted so as to modify the saturation concentration of the drug in the polymer matrix in order to affect the rate of delivery of the drug from the system and through the skin. In some embodiments, the acrylic-based polymer and silicone-based polymer are used in a weight ratio of from about 2:98 to about 96:4, including about 2:98 to about 90:10 and 2:98 to about 86:14, such as 2:98 to 96:4, 2:98 to 90:10 and 2:98 to 86:14.

The concentration by weight of the estrogen in the transdermal drug delivery system is typically about 0.1 to about 50%, including about 0.1 to about 40% and about 0.3 to about 30%, such as 0.1 to 50%, 0.1 to 40% and 0.3 to 30%, all based on the total weight of the polymer matrix. In some embodiments, the estrogen is estradiol, and is present at an amount of from about 0.1 to 10%, including from about 0.1 to about 5%, such as from 0.1 to 10% and 0.1 to 5%, all based on the total weight of the polymer matrix. Irrespective of whether there is high-loading or low-loading of the estrogen into the transdermal drug delivery system, the pressure-sensitive adhesive composition can be formulated to maintain acceptable shear, tack, and peel adhesive properties.

Other Components

In one embodiment, the polymer matrix comprises a penetration enhancer. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skirt including the boundary layer.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyidecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In one embodiment, the penetration enhancer is oleyl alcohol. In another embodiment, the penetration enhancer is a glycol, such as dipropylene glycol, propylene glycol, butylene glycol or polyethylene glycol. In other embodiments, the penetration enhancer comprises a mixture of at least two penetration enhancers. For example, a penetration enhancer may comprise oleyl alcohol and one or more polyhydric alcohols, such as glycerine, dipropylene glycol, butylene glycol, propylene glycol. For instance, the penetration enhancer may include oleyl alcohol and dipropylene glycol.

In some embodiments, a penetration enhancer is used in an amount up to about 30% by dry weight of the polymer matrix, including up to 30% by weight, up to about 20% by weight, including 20% by weight, or up to about 10% by weight, up to 10% by weight, or up to 5% by weight, including up to 5% by weight, based on the dry weight of the polymer matrix. In some embodiments, a penetration enhancer is used in an amount of from about 5% to about 15%, such as from 5% to 15%. In specific embodiments, the penetration enhancer comprises a mixture of oleyl alcohol and dipropylene glycol which together amount to about 14% by weight of the polymer matrix. The polymer matrix may further comprise various thickeners, fillers, and other additives or components known for use in transdermal drug delivery systems.

The amount of estrogen to be incorporated in the polymer matrix varies depending on the particular drug, the desired therapeutic effect, and the time span for which the system is to provide therapy. For most drugs, the passage of the drugs through the skin will be the rate-limiting step in delivery. A minimum amount of drug in the system is selected based on the amount of drug which passes through the skin in the time span for which the system is to provide therapy. In some embodiments, a system for the transdermal delivery of estrogen is used over a period of about 1 day, about 3 days, about 7 days, or longer. Thus, in one embodiment, the systems comprise an amount of drug (e.g., estradiol) sufficient to deliver therapeutically effective amounts of drug over a period of from 1 day to 3 days, 7 days, or longer, including for 1 day, for 2 days, for 3 days, for 4 days, for 5 days, for 6 days, for 7 days, or for longer. In some embodiments, a therapeutically effective amount of estradiol is from about 0.025-0.1 mg/day, including about 0.025 mg/day, about 0.0375 mg/day, about 0.05 mg/day, about 0.075 mg/day, or about 0.1 mg/day, such as 0.025-0.1 mg/day, 0.025 mg/day, 0.0375 mg/day, 0.05 mg/day, 0.075 mg/day, and 0.1 mg/day. Thus, in some embodiments, the transdermal drug delivery system comprises an amount of estradiol effective to achieve a delivery of from at least about 0.025 mg to at least about 0.1 mg of estradiol per day. In some embodiments, the system comprises an amount of estradiol effective to achieve a delivery of from about 0.025 mg to about 0.1 mg of estradiol per day, including about 0.025 mg/day, about 0.0375 mg/day, about 0.05 mg/day, about 0.075 mg/day, or about 0.1 mg/day, such as 0.025-0.1 mg/day, 0.025 mg/day, 0.0375 mg/day, 0.05 mg/day, 0.075 mg/day, and 0.1 mg/day. As noted above, in some embodiments, these rates are achieved over a duration of application of at least about 1 day, including at least about 3 days and at least about 7 days, such as at least 1 day, at least 2 days, at least 3 days, at least 4 days, at least 5 days, at least 6 days, and at least 7 days. Thus, for example, transdermal drug delivery system may comprise from at least about 0.39 mg to at least about 1.56 mg estradiol, including about 0.39 mg, about 0.585 mg, about 0.78 mg, about 1.17 mg, and about 1.56 mg, such as 0.39 mg, about 0.585 mg, about 0.78 mg, about 1.17 mg, and about 1.56 mg. In some embodiments, the transdermal drug delivery system comprises a smaller amount of estradiol than a Vivelle-Dot® product, but achieves comparable drug delivery. For example, in some embodiments a transdermal drug delivery system according to the invention may contain about 1.44 mg or about 1.2 mg estradiol in a 6 $cm^2$ device, and achieve drug delivery comparable to a Vivelle-Dot® product that contains about 1.56 mg estradiol in a 10 $cm^2$ device.

In some embodiments, the system comprises a polymer matrix comprising an amount of acrylic-based polymer of about 1 to about 70% by weight, including about 2 to about 25% by weight, based on the dry weight of the polymer matrix, such as 2-25% by weight acrylic-based polymer.

In some embodiments, the system comprises a polymer matrix comprising an amount of silicone polymer of about 5 to about 70% by weight, including about 45 to about 70% by weight, based on the dry weight of the polymer matrix, such as 45-70% by weight silicone polymer.

In some embodiments, the system comprises a polymer matrix comprising an amount of soluble PVP of about 1 to about 30% by weight, including about 2 to about 25% by weight, based on the dry weight of the polymer matrix, such as 2-25% by weight soluble PVP.

In some embodiments, the system comprises a polymer matrix comprising an amount of oleyl alcohol of about 1 to about 10% by weight, including about 4 to about 8% by weight, based on the dry weight of the polymer matrix, such as 4-8% by weight oleyl alcohol.

In some embodiments, the system comprises a polymer matrix comprising an amount of dipropylene glycol of about 1 to about 10% by weight, including about 5 to about 10% by weight, based on the dry weight of the polymer matrix, such as 5-10% by weight dipropylene glycol.

In some embodiments, the polymer matrix comprises about 2-25% by weight acrylic adhesive, about 45-70% by weight silicone adhesive, about 2-25% by weight soluble PVP, about 5-15% penetration enhancer, and about 0.1-10% by weight estradiol, all based on the total dry weight of the polymer matrix. In specific embodiments, the polymer matrix comprises about 20% by weight acrylic adhesive, about 56.9% by weight silicone adhesive, about 7.5% by weight soluble PVP, about 6.0% by weight oleyl alcohol, about 8.0% by weight dipropylene glycol, and about 1.6% by weight estradiol.

In some embodiments, the acrylic adhesive and silicone adhesive are present in a ratio of from about 1:2 up to less than about 1:7, such as up to about 1:6, based on the weight of the acrylic and silicone adhesives. For example, in some embodiments, the acrylic adhesive and silicone adhesive are present in a ratio of about 1:2, 1:3, 1:4, 1:5 or 1:6, based on the weight of the acrylic and silicone adhesives. In specific embodiments, the acrylic adhesive and silicone adhesive are present in a ratio of 1:2.8, based on the weight of the acrylic and silicone adhesives.

As noted above, in embodiments where the polymer matrix comprises a pressure-sensitive adhesive or bioadhesive, the polymer matrix can serve as an adhesive portion of the system (e.g., a reservoir device), or can serve as one or more layers of a multi-layer system. Alternatively, a polymer matrix comprising a pressure-sensitive adhesive or bioadhesive with drug dissolved or dispersed therein can constitute a monolithic device. In embodiments where the polymer matrix does not comprise an adhesive, but instead, for example, comprises a polymeric drug reservoir, it can be used in combination with one or more adhesive layers, or with a surrounding adhesive portion, as is well known to those skilled in the art.

In some embodiments, the system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

As discussed above, in some embodiments, the systems have a greater flux than other known estrogen devices (such as Vivelle-Dot®, manufactured by Noven Pharmaceuticals Inc.), and, therefore, exhibit increased drug delivery per unit area of the active surface area. For example, in some embodiments, the systems exhibit a flux greater than the 0.01 mg/cm$^2$/day exhibited by the Vivelle-Dot® products, such as a flux that is about 1.25, 1.33, 1.5, 1.67, 1.75, 2, 3, 4, or 5 times the flux of the Vivelle-Dot® products. In specific embodiments, the systems exhibit a flux that is about 1.67 times the flux of the Vivelle-Dot® products, e.g., a flux that is about 0.0167 mg/cm$^2$/day.

In some embodiments, the systems have a greater coat weight than other known estrogen devices. For example, in some embodiments, the systems have a coat weight such that the amount of estradiol per unit area of the active surface area is greater than the 0.156 mg/cm$^2$ estradiol of the Vivelle-Dot® products, such as a coat weight that is about 1.25, 1.33, 1.5, 1.67, 1.75, 2 or 3 times the coat weight of the Vivelle-Dot® products, or greater. In specific embodiments, the systems have a coat weight that is about 1.25 times the coat weight of the Vivelle-Dot® products, e.g., a coat weight of about 12.5 mg/cm$^2$. In other specific embodiments, the systems have a coat weight that is about 1.5 times the coat weight of the Vivelle-Dot® products, e.g., a coat weight of about 15 mg/cm$^2$.

The system may be of any shape or size suitable for transdermal application. In some embodiments, the systems are smaller than the Vivelle-Dot® products, but achieve comparable daily dosages. For example, the systems may have an active surface area of 0.9, 0.8, 0.7, 0.75, 0.66, 0.6, 0.5, 0.4, 0.33, 0.3, 0.25, 0.2, or 0.1 times the active surface area of a Vivelle-Dot® product. In some embodiments, the system has an active surface area that is about 60% the size of a Vivelle-Dot® product, such as about 60% of 2.5, 3.75, 5.0, 7.5 or 10.0 cm$^2$, and delivers a daily dosage of estradiol comparable to that of the corresponding Vivelle-Dot® product. In one embodiment, the system has an active surface area of about 6 cm$^2$ and delivers a daily dosage of estradiol comparable to that of the 10 cm$^2$ Vivelle-Dot® product, e.g., about 0.1 mg/day.

The polymer matrices described herein may be prepared by methods known in the art. The polymer matrices can be formed into systems by methods known in the art. For example, the polymer matrix material can be applied to a backing layer and release liner by methods known in the art, and formed into sizes and shapes suitable for use.

For example, after the polymer matrix is formed, it may be brought into contact with a support layer, such a releaser liner layer or backing layer, in any manner known to those of skill in the art. Such techniques include calender coating, hot melt coating, solution coating, etc.

For example, a polymer matrix can be prepared by blending the components of the polymer matrix, applying the matrix material to a support layer such as a backing layer or release liner, and removing any remaining solvents. The estrogen can be added at any stage. In one embodiment, all polymer matrix components, including estrogen, are blended together. In another embodiment, the polymer matrix components other than estrogen are blended together, and then the estrogen is dissolved or dispersed therein. The order of steps, amount of ingredients, and the amount and time of agitation or mixing can be determined and optimized by the skilled practitioner. An exemplary general method is as follows:

Appropriate amounts of soluble PVP, solvent(s), enhancer(s), and organic solvent(s) (for example toluene) are combined and thoroughly mixed together in a vessel.

Estrogen is then added to the mixture and agitation is carried out until the drug is uniformly mixed in.

Appropriate amounts of polysiloxane and acrylic polymer are then added to the drug mixture, and thoroughly mixed.

The formulation is then transferred to a coating operation where it is coated onto a protective release liner at a controlled specified thickness. The coated product is then passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

In some embodiments, there is provided a method of effecting transdermal drug delivery of estrogen, such as estradiol, by applying a system as described herein to the skin or mucosa of a subject in need thereof. In some embodiments, the system comprises estradiol, and the system is applied over a period of at least about 1 day, at least about 2 days, at least about 3 days, at least about 4 days, at least about 5 days, at least about 6 days, or at least about 7 days, such as for 1, 2, 3, 4, 5, 6 or 7 days. In some embodiments, the method is effective to achieve therapeutic levels of estrogen in the subject during the application period. As noted above, a typical dosage ranges from at least about 0.025 mg to at least about 0.1 mg of estradiol per day, such as from about 0.025 mg to about 0.1 mg of estradiol per day, including about 0.025 mg/day, about 0.0375 mg/day, about 0.05 mg/day, about 0.075 mg/day, or about 0.1 mg/day, such as 0.025-0.1 mg/day, 0.025 mg/day, 0.0375 mg/day, 0.05 mg/day, 0.075 mg/day, and 0.1 mg/day.

The following specific examples are included as illustrative of the transdermal drug delivery systems and polymer matrices described herein. These example are in no way intended to limit the scope of the invention. Other aspects of the invention will be apparent to those skilled in the art to which the invention pertains.

EXAMPLE 1

A polymer matrix with the following composition is prepared:

| | |
|---|---|
| Acrylic Adhesive | 20% |
| Silicone Adhesive | 56.9% |
| Povidone (PVP) | 7.5% |
| Oleyl Alcohol | 6.0% |
| Dipropylene Glycol, USP | 8.0% |
| Estradiol | 1.6% |

(all % are % by weight based on the dry weight of the total polymer matrix)

The polymer matrix is applied to a release liner at a coat weight of 12.5 (●) or 15 (▲) mg/cm$^2$.

Human cadaver skin permeation studies were performed to quantitatively determine the effective permeation through the stratum corneum. The stratum corneum was obtained from split thickness, cryo-preserved cadaver skin by the heat separation technique. Samples of 5/16" diameter were cut from the laminate, in quadruplicate, and mounted onto ½" cut pieces of the stratum corneum. These samples were then placed on modified Franz diffusion cells. The receptor was filled with 7.5 mL of 0.9% NaCl and 0.01% $NaN_3$ in deionized water. The cells were maintained at a constant 32° C. and were magnetically stirred at approximately 300 rpm. At specified time points, samples of the receptor phase were taken with complete replacement of the receptor phase. These samples were quantified by high-performance liquid chromatography (HPLC) utilizing Waters HPLC instrumentation. C-8 (15 cm×4.6 mm) 5 μm particle size columns (HYPERSIL made by MetaChem Technologies, Inc., Torrance, Calif.) were used at 50° C. (column temperature).

FIG. 1 illustrates the estradiol flux (μg/cm$^2$/hr) over time (0-81 hours) from transdermal delivery systems according to the invention (▲ & ●), as compared to Vivelle-Dot® (♦).

The results show that the systems according to the invention have a greater flux than the Vivelle-Dot® product and are able to achieve therapeutic daily dosages despite their significantly smaller size.

What is claimed is:

1. A monolithic transdermal drug delivery system for estradiol, consisting of (i) a backing layer, (ii) a single adhesive polymer matrix layer defining an active surface area and, optionally, (iii) a release liner, wherein the single adhesive polymer matrix layer comprises an adhesive polymer matrix comprising estradiol as the only drug, wherein the adhesive polymer matrix layer has a coat weight of greater than 10 mg/cm$^2$ and includes greater than 0.156 mg/cm$^2$ estradiol, and the system achieves an estradiol flux of from 0.0125 to about 0.05 mg/cm$^2$/day, based on the active surface area.

2. The transdermal drug delivery system of claim 1, wherein the adhesive polymer matrix comprises a polymer blend comprising an acrylic adhesive, a silicone adhesive, and soluble PVP.

3. The transdermal drug delivery system of claim 1, wherein the adhesive polymer matrix comprises about 2-25% by weight acrylic adhesive, about 45-70% by weight silicone adhesive, about 2-25% by weight soluble PVP, about 5-15% penetration enhancer, and about 0.1-10% by weight estradiol, all based on the total dry weight of the adhesive polymer matrix.

4. The transdermal drug delivery system of claim 3, wherein the penetration enhancer comprises oleyl alcohol.

5. The transdermal drug delivery system of claim 3, wherein the penetration enhancer comprises dipropylene glycol.

6. The transdermal drug delivery system of claim 3, wherein the penetration enhancer comprises oleyl alcohol and dipropylene glycol.

7. The transdermal drug delivery system of claim 3, wherein the acrylic adhesive and silicone adhesive are present in a ratio of from about 1:2 to about 1:6, based on the total weight of the acrylic and silicone adhesives.

8. The transdermal drug delivery system of claim 1, wherein the adhesive polymer matrix comprises an amount of estradiol effective to deliver a therapeutically effective amount of estradiol over a period of time selected from the group consisting of at least 1 day, at least 2 days, at least 3 days, at least 4 days, at least 5 days, at least 6 days and at least 7 days.

9. The transdermal drug delivery system of claim 1, wherein the adhesive polymer matrix comprises an amount of estradiol effective to deliver an amount of estradiol selected from the group consisting of about 0.025, 0.0375, 0.05, 0.075 and 0.1 mg/day.

10. The transdermal drug delivery system of claim 1, wherein the system achieves an estradiol flux of 0.0125 mg/cm$^2$/day, based on the active surface area.

11. The transdermal drug delivery system of claim 1, wherein the system achieves an estradiol flux of 0.0133 mg/cm$^2$/day, based on the active surface area.

12. The transdermal drug delivery system of claim 1, wherein the system achieves an estradiol flux of about 0.015 mg/cm$^2$/day, based on the active surface area.

13. The transdermal drug delivery system of claim 1, wherein the system achieves an estradiol flux of about 0.0167 mg/cm$^2$/day, based on the active surface area.

14. The transdermal drug delivery system of claim 1, wherein the system achieves an estradiol flux of about 0.0175 mg/cm $^2$/day, based on the active surface area.

15. The transdermal drug delivery system of claim 1, wherein the adhesive polymer matrix comprises about 1.6% by weight estradiol, based on the total dry weight of the adhesive polymer matrix.

* * * * *